United States Patent [19]

Jensen et al.

[11] Patent Number: 4,820,736
[45] Date of Patent: Apr. 11, 1989

[54] USE OF CLOMIPHENE TO PREDICT FERTILITY IN A HUMAN FEMALE

[75] Inventors: Pamela S. Jensen, Camden, Me.; Florence Comite, New Haven, Conn.

[73] Assignee: Yale University, New Haven, Conn.

[21] Appl. No.: 28,371

[22] Filed: Mar. 20, 1987

[51] Int. Cl.$^4$ .......................................... A61K 31/135
[52] U.S. Cl. ...................................... 514/651; 514/899
[58] Field of Search .............................. 514/651, 899

[56] References Cited

U.S. PATENT DOCUMENTS 4,729,999   3/1988   Young .................................. 514/227

FOREIGN PATENT DOCUMENTS 1146405   3/1969   United Kingdom ................. 514/651

OTHER PUBLICATIONS

Chemical Abstract #100:132789g (1984).
Chemical Abstract #89:21040r (1977).
Chemical Abstract #85:72785n (1976).
Chemical Abstract #98:83774c (1982).
Chemical Abstract #84:174381z (1976).
A. Horsman, B. E. C. Nordin, J. C. Gallagher et al, "Observations of Sequential Changes in Bone Mass in Postmenopausal Women: A Controlled Trial of Estrogen and Calcium Therapy", *Calcif. Tissue Res.*, 22, (suppl) 217–224, (1977).
F. L. Geola, A. M. Frumar, I. V. Tataryn et al "Biological Effects of Various Doses of Conjugated Equine Estrogens in Postmenopausal Women", *Clin. Endocrinol. Metab.*, 51, 620–625, (1980).
B. Riis, K. Thomsen and C. Christiansen, "Does Calcium Supplementation Prevent Postmenopausal Bone Loss? A Double-blind, Controlled Study", *N. Engl. J. Med.*, 316, 173–177, (1987).
E. Kokko, O. Janne, A. Kauppila et al, "Cyclic Clomiphene Citrate Treatment Lowers Cytosol Estrogen and Progestin Receptor Concentrations in the Endometrium of Postmenopausal Women on Estrogen Replacement Therapy", *J. Clin. Endocrinol. Metab.*, 52, 345–349, (1981).
P. T. Beall, L. K. Misra, R. L. Young, H. J. Spjut, H. J. Evans and LeBlanc, "Clomiphene Protects Against Osteoporosis in the Mature Ovariectomized Rat", *Calcif. Tissue Int.*, 36, 123, (1984).
P. J. Stewart and P. H. Stern, "Effects of the Antiestrogens Tamoxifen and Clomiphene on Bone Resorption In Vitro", *Endocrinol.*, 118, 125–131, (1986).
G. D. Hodgen, A. L. Goodman, A. O'Connor et al, "Menopause in Rhesus Monkeys: Model for Study of Disorders in the Human Climacteric", *Am. J. Obstet. Gynecol.*, 127, 581–584, (1977).
J. A. Wall, R. R. Franklin and R. H. Kaufman, "Reversal of Benign and Malignant Endometrial Changes with Clomiphene", *Am. J. Obstet. Gynecol.*, 88, 1072, (1964).
C. Christiansen, R. B. Mazess, I. Transbol and G. F. Jensen, "Factors in Response to Treatment of Early Postmenopausal Bone Loss", *Calcif. Tissue Int.*, 33, 575, (1981).
S. Meema, M. L. Bunker and H. E. Meema, "Preventive Effect of Estrogen on Postmenopausal Bone Loss", *Arch. Intern Med.*, 135, 1436, (1975).
B. E. C. Nordin, A. Horsman, R. G. Grilly et al, "Treatment of Spinal Osteoporosis in Postmenopausal Women", *Br. Med. J.*, 280, 451–454, (1980).
B. L. Riggs, J. Jowsey, R. S. Goldsmith, P. J. Kelly, D. L. Hoffman and C. D. Arnaud, "Short and Long Term Effects of Estrogen and Synthetic Anabolic Hormone in Postmenopausal Osteoporosis", *Clin. Invest.*, 51, 1659, (1972).
F. W. Lafferty, G. E. Spencer and O. H. Pearson, "Effects of Androgens, Estrogens and High Calcium Intakes on Bone Formation and Resorption in Osteoporosis"*Am. J. Med.*, 36, 514 (1964).
C. Christiansen, M. S. Christensen, P. McNair, C. Hagen, K.-E. Stocklun and I. Transbol, "Prevention of Early Postmenopausal Bone Loss: Controlled 2-year Study in Normal Females", *Eur. J. Clin. Invest.*, 10, 273, (1980).
Clinics in Obstetrics & Gynaecology, vol. 4, No. 1, Apr. 1977, pp. 31–47 "Oestrogen Therapy and the Menopausal Syndrome", Stuart Campbell & Malcolm Whitehead.
Rafat Abbasi, Gary D. Hodgen, Predicting the Predisposition of Osteoporosis, JAMA, Mar. 28, 1986, vol. 255, No. 12 pp. 1600–1604 and 1614 and 1615.

*Primary Examiner*—Albert T. Meyers
*Assistant Examiner*—Freda L. Krosnick
*Attorney, Agent, or Firm*—Sprung Horn Kramer & Woods

[57] ABSTRACT

The invention relates to the use of clomiphene and its citrate salt in predicting fertility in a human female.

2 Claims, No Drawings

USE OF CLOMIPHENE TO PREDICT FERTILITY IN A HUMAN FEMALE

BACKGROUND OF THE INVENTION

1. Field of the Invention

The present invention concerns the use of clomiphene to increase bone mass, i.e., to treat and/or prevent osteoporosis, in humans.

2. Background Information

Osteoporosis is a condition wherein the patient suffers from decreased bone mass, involving loss of both mineral and protein matrix components. Osteoporosis occurs in patients suffering from estrogen deficit (postmenopausal), catabolic hormone excess (e.g., Cushing's disease), long-term administration of corticosteroids in large doses, immobilization, liver disease, gonadal dysgenesis and osteogenesis imperfecta. The chief complications of osteoporosis are bone pain, fracture, kyphosis and invalidism. More common in females than in males and in Caucasians than in Negroes, osteoporosis is rarer in premenopausal women.

In most cases, especially in the postmenopausal form, symptoms begin with pain in the weight-bearing vertebrae, i.e., T-8 and below. It is usually localized in the vertebrae, does not radiate and is not associated with generalized bone tenderness. Local tenderness is present if fracture occurs. Loss of height may result from multiple vertebral fractures and kyphosis and can be confirmed by disparity between the height and span in the absence of other causes for such disparity (e.g., arachnodactyly or eunuchoidism). Serum calcium and alkaline phosphatase levels are normal; serum phosphorus may be slightly elevated in postmenopausal women and in hyperthyroid patients, but low in Cushing's disease.

Osteoporosis is generally detected by x-ray examination. The vertebrae show loss of trabecular structure, increased contrast between the relatively preserved cortex and more seriously involved spongiosa, biconcavity, Schmorl's nodules and wedge fractures with the apex anterior. Reliance on subjective impressions of bone density if often misleading. Eburnation or thickening of the superior and inferior vertebral plates distinguishes the osteoporosis of Cushing's disease or of corticosteroid therapy from other varieties. Corticosteroid-induced osteoporosis is more likely to produce rib fractures and exuberant callus formation.

Heretofore, treatment of osteoporosis was both supportive and specific. The patient was instructed to remain as active as possible and in some instances the patient required a supporting corset. Correction of the underlying cause usually stops progression of the disease, but does not restore bone mass except in the cure of Cushing's disease in children. Treatment for the most common form of osteoporosis (i.e., in postmenopausal women) has been the subject of much controversy. Cyclic estrogen administration orally (conjugated estrogens 1.25 mg, or diethylstilbestrol 0.5 mg, or ethinyl estradiol 0.05 mg, once/day omitting 5 days each month) often relieves pain and was heretofore the only long-term therapy reported to prevent further fractures. Since x-rays show no restoration of bone mass, large doses of calcium (2 to 6 Gm/day orally), vitamin D, or fluoride have been tried. Subjective improvement and positive calcium balance have been reported. However, phosphate is not retained, indicating that bone mineral is not deposited; others report no significant calcium retention. Fluoride has been advocated on epidemiologic grounds, since bones appear more dense in areas where the water contains large amounts of fluoride. Fluorosis, however, produces brittle bones and ectopic calcification; and calcium in large doses may cause hypercalciuria and kidney stones. Moreover, unlike estrogens, neither has been shown to stop further fractures of postmenopausal osteoporosis. High doses of calcium and treatment with fluoride, therefore, must be considered investigational. Calcitonin, which inhibits bone resorption, has not been adequately evaluated. Androgen and other anabolic steroid therapy are no longer considered advisable because of undesirable virilization.

Estrogens have a profound effect on bone homeostasis, (B. L. Riggs, J. Jowsey, R. S. Goldsmith, P. J. Kelly, D. L. Hoffman and C. D. Arnaud, "Short and Long Term Effects of Estrogen and Synthetic Anabolic Hormone in Postmenopausal Osteoporosis", *Clin. Invest.*, 51, 1659, (1972) and F. W. Lafferty, G. E. Spencer and O. H. Pearson, "Effects of Androgens, Estrogens and High Calcium Intakes on Bone Formation and Resorption in Osteoporosis, *Am. J. Med.*, 36, 514, (1964)), although the mechanisms by which estrogens actually produce their effects on the bone have not been determined. Estrogens are well known to be potent therapeutic agents in the prevention of progressive bone mass reduction in osteoporotic women after the onset of menopause, (C. Christiansen, M. S. Christensen, P. McNair, C. Hagen, K.-E. Stocklun and I. Transbol, "Prevention of Early Postmenopausal Bone Loss: Controlled 2-year Study in 315 Normal Females", *Eur. J. Clin. Invest.*, 10, 273, (1980); C. Christiansen, R. B. Mazess, I. Transbol and G. F. Jensen, "Factors in Response to Treatment of Early Postmenopausal Bone Loss", *Calcif. Tissue Int.*, 33, 575, (1981); S. Meema, M. L. Bunker and H. E. Meema, "Preventive Effect of Estrogen on Postmenopausal Bone Loss", *Arch. Intern Med.*, 135, 1436, (1975); B. E. C. Nordin, A. Horsman, R. G. Grilly et al, "Treatment of Spinal Osteoporosis in Postmenopausal Women", *Br. Med. J.*, 280, 451–454, (1980); A. Horsman, B. E. C. Nordin, J. C. Gallagher et al, "Observations of Sequential Changes in Bone Mass in Postmenopausal Women: A Controlled Trial of Estrogen and Calcium Therapy", *Calcif. Tissue Res.*, 22, (suppl) 217–224, (1977); S. Campbell and M. Whitehead, "Estrogen Therapy and the Postmenopausal Syndrome", *Clin. Obstet. Gynecol.* 4, 1–30, (1977); F. L. Geola, A. M. Frumar, I. V. Tataryn et al, "Biological Effects of Various Doses of Conjugated Equine Estrogens in Postmenopausal Women", *Clin. Endocrinol. Metab.*, 51, 620–625, (1980) and B. Riis, K. Thomsen and C. Christiansen, "Does Calcium Supplementation Prevent Postmenopausal Bone Loss? A Double-blind, Controlled Study", *N. Engl. J. Med.*, 316, 173–177, (1987)).

Clomiphene is a drug that is used to induce ovulation in infertile women. It is a competitive antagonist to estrogen. While clomiphene displays some anti-estrogenic properties, it also has estrogenic properties depending upon specie and tissue. Since clomiphene has a negative effect upon the endometrium, causing it to become atrophic, (E. Kokko, O Janne, A. Kauppila et al, "Cyclic Clomiphene Citrate Treatment Lowers Cytosol Estrogen and Progestin Receptor Concentrations in the Endometrium of Postmenopausal Women on Estrogen Replacement Therapy", *J. Clin. Endo-* crinol. Metab., 52, 345–349, (1981)), it was heretofore believed that clomiphene also has a negative effect on bone mass in humans.

Animal studies have shown that clomiphene prevents deterioration of the femoral bone in adult ovariectomized rats, (P. T. Beall, L. K. Misra, R. L. Young, H. J. Spjut, H. J. Evans and LeBlanc, "Clomiphene Protects Against Osteoporosis in the Mature Ovariectomized Rat", *Calcif. Tissue Int.*, 36, 123, (1984)). Likewise, clomiphene and tamoxifen (also an estrogen agonist-antagonist) have been shown to completely block parathyroid-induced bone resorption in vitro, (P. J. Stewart and P. H. Stern, "Effects of the Antiestrogens Tamoxifen and Clomiphene on Bone Resorption In Vitro", *Endocrinol.*, 118, 125–131, (1986)). High doses of clomiphene have been reported to be effective as high-dose conjugated equine estrogens for conservation of urinary calcium in a primate model, (G. D. Hodgen, A. L. Goodman, A. O'Connor et al, "Menopause in Rhesus Monkeys: Model for Study of Disorders in the Human Climacteric", *Am. J. Obstet. Gynecol.*, 127, 581–584, (1977)). Consequently, it appears that clomiphene in humans may also act as an estrogen at certain target cells such as bone, while acting as an anti-estrogen on other cells such as the endometrium. Importantly, unlike estrogen, clomiphene does not induce mitogenic effects on uterine endometrium, (J. A. Wall, R. R. Franklin and R. H. Kaufman, "Reversal of Benign and Malignant Endometrial Changes with Clomiphene", *Am. J. Obstet. Gynecol.*, 88, 1072, (1964)).

SUMMARY OF THE INVENTION

The present invention is directed to a method for increasing bone mass in humans comprising administering to a human patient an effective amount of clomiphene, either alone or in admixture with a diluent or in the form of a medicament.

The present invention is thus directed to a treatment and/or prevention of osteoporosis in humans.

Still further, the present invention concerns a method for predicting fertility in a human female comprising administering an effective amount of clomiphene to the female and determining if the female experiences increased bone mass.

DETAILED DESCRIPTION OF THE INVENTION

The structure of clomiphene, 2-[4-(2-chloro-1,2-diphenylethenyl)-phenoxy]-N,N-diethylethanamine; 2-[p-(2-chloro-1,2-diphenylvinyl)phenoxy]triethylamine; 2-[p-($\beta$-chloro-$\alpha$-phenylstyryl)phenoxy]triethylamine; 1-[p-($\beta$-diethylaminoethoxy)phenyl]-1,2-diphenylchloroethylene; clomifene; chloramiphene; $C_{26}H_{28}ClNO$; mol. wt. 405.98, is as follows:

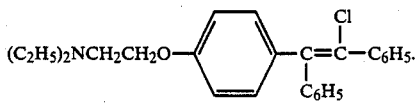

Allen et al, U.S. Pat. No. 2,914,563 describes the preparation of clomiphene.

Clomiphene as used in this invention can also be utilized in its citrate form, i.e., clomiphene citrate.

Clomiphene binds to the estrogen receptors and acts by stimulating the hypothalmic-pituitary-ovarian axis in a similar fashion as estrogen.

The effectiveness of clomiphene in inducing ovulation relates to its ability to bind to the estrogen receptor for a prolonged period as opposed to naturally occurring estrogen. The hypothalamic-pituitary axis is then able to initiate the pre-ovulatory LH surge necessary for ovulation to occur.

Without wishing to be bound by any theory of operability, it is believed that clomiphene may act either indirectly via the hypothalamic-pituitary axis to promote increased bone formation, or directly on the bone itself in humans.

Based on animal studies it was believed that clomiphene would decrease bone mass. The applicants, however, have discovered that clomiphene actually increases bone mass in humans. Clomiphene can, therefore, be utilized to treat disorders where decreased bone mass is a consequence, such as osteoporosis. Clomiphene can also be used prophylactically to increase bone mass prior to the menopausal period, thereby avoiding the development of postmenopausal osteoporosis or decreasing the magnitude of the associated bone loss. Clomiphene may also be used as a marker of potential fertility since increased bone formation occurs primarily in women who are capable of sustaining a pregnancy, but may not in women who remain infertile despite clomiphene therapy.

Clomiphene is presently sold by Merrell Dow Pharmaceuticals Inc., Indianapolis, Indiana, under the name "CLOMID" and by Serono under the name "SEROPHENE". Clomiphene is also sold under the names "CLOMPHID", "CLOMIVID", "CLOSTILBEGYT", "DYNERIC" and "IKACLOMINE".

Clomiphene can be utilized in the present invention as a pharmaceutical composition containing clomiphene (the active ingredient) in admixture with a solid, liquid or liquefied gaseous diluent.

Clomiphene may also be utilized as a pharmaceutical composition in the form of a sterile and/or physiologically isotonic aqueous solution.

Clomiphene may also be used as a medicament in dosage unit form or as a medicament in the form of tablets (including lozenges and granules), caplets, dragees, capsules, pills, ampoules or suppositories.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the compound of the invention in association with a carrier and/or enclosed within an envelope. Whether the medicament contains a daily dose, or for example, a half, a third or a quarter of a daily dose will depend on whether the medicament is to be administered once or, for example, twice, three times or four times a day, respectively.

The pharmaceutical compositions according to the invention may, for example, take the form of suspensions, solutions and emulsions of the clomiphene in aqueous or non-aqueous diluents, syrups, granulates or powders.

The diluents to be used in pharmaceutical compositions (e.g., granulates) adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agaragar, calcium carbonate and sodium bicarbonate; (e) agents for retarding dissolution, e.g., paraffin; (f) resorption accelerators, e.g, quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethyl glycols.

The tablets, dragees, capsules, caplets and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

Clomiphene can also be made up in microencapsulated form together, with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and emulsions should be sterile and, if appropriate, blood-isotonic.

The pharmaceutical compositions which are suspensions can contain the usual diluents, such as liquid diluents, e.g., water, ethyl alcohol, propylene glycol, surface-active agents (e.g., ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions for use in the invention can also contain coloring agents and preservatives, as well as perfumes and flavoring additions (e.g., peppermint oil and eucalyptus oil) and sweetening agents (e.g., saccharin and aspartame).

The pharmaceutical compositions for use in the invention generally contain from 0.5 to 90% of clomiphene by weight, relative to the weight of the total composition.

In addition to clomiphene, the pharmaceutical compositions and medicaments used according to the invention can also contain other pharmaceutically active compounds.

Any diluent in the medicaments of the present invention may be any of those mentioned above in relation to the pharmaceutical compositions for use in the present invention. Such medicaments may include solvents of molecular weight less than 200 as the sole diluent.

The discrete coherent portions constituting the medicament for use in the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, may include a protective envelope which renders the portions of the medicament physically discrete and coherent.

The preferred daily dose for administration of the medicaments for use in the invention is 2.5 to 250 mg of clomiphene in the case of intravenous administration and 25 to 250 mg, preferably 150 mg, of clomiphene in the case of oral administration. The drug is generally administered for a portion of every month, but can be administered daily.

The product of the above-mentioned pharmaceutical compositions and medicaments is carried out by any method known in the art, for example, by mixing the clomiphene with the diluents(s) to form a pharmaceutical composition (e.g., a granulate) and then forming the composition into the medicament (e.g. tablets).

This invention provides a method for treating the above-mentioned diseases in humans, which comprises administering clomiphene to a human, alone or in admixture with a diluent or in the form of a medicament according to the invention.

It is envisaged that clomiphene will be administered perorally, parenterally (for example, intramuscularly, intraperitoneally, subcutaneously or intravenously), rectally, vaginally or locally, preferably orally or parenterally. Preferred pharmaceutical compositions and medicaments are, therefore, those adapted for administration such as oral or parenteral administration. Administration in the method of the invention is preferably oral. Clomiphene can also be administered via a depot formulation, e.g., a slow release form placed subcutaneously and/or intramuscularly.

In general, it has proved advantageous to administer intravenously amounts of from 0.01 mg to 10 mg/kg, preferably 0.05 to 5 mg/kg, of body weight per day and to administer orally 0.05 to 20 mg/kg, preferably 0.5 mg to 5 mg/kg of body weight per day, to achieve effective results. Nevertheless, it can at times be necessary to deviate from those dosage rates, and in particular to do so as a function of the nature and body weight of the human subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than the above-mentioned minimum dosage rate, whilst other cases the upper limit mentioned must be exceeded to achieve the desired results. Where larger amounts are administered, it may be advisable to divide these into several individual administrations over the course of the day.

Clomiphene may be used in the present invention as an effective estrogen alternative for action on bone, without the estrogenic side effects at other sites. Clomiphene could be the ideal hormonal replacement for postmenopausal women who have or are at risk for endometrial and breast carcinoma, preserving the skeleton while reducing the risk of cancer.

Clomiphene may be used in the present invention (a) to treat decreased bone mass,
(b) to increase bone mass prior to an anticipated loss of bone thereby preventing osteoporosis or decreasing the magnitude of bone loss or
(c) as a marker of potential fertility, since it appears that women with normal reproductive capacities primarily experience the increased bone mass following clomiphene therapy.

Although this invention may be used to predict fertility in women with noraml reproductive capabilities, clomiphene may also be utilized according the present invention to treat osteoporosis in perimenopausal and postmenopausal women in which fertility is not a consideration.

The invention will now be described with reference to the following non-limiting examples.

EXAMPLES

Example 1

Quantitative computer tomography (QCT) of distal radius described in P. S. Jensen, S. C. Orphanoudakis, E. N. Rauschkolb, R. Baron, R. Lang and H. Rasmussen, "Assessment of Bone Mass in the Radius by Computed Tomography", *American Journal of Radiology*, 134, 285-292, (1980) was used to measure bone mass in twenty women with endometriosis. It was found that trabecular mass was normal in the seventeen women with endometriosis and increased in three women. In addition, these three women with significantly increased trabecular bone mass had been treated with the drug "CLOMID" (clomiphene) in the past. Trabecular bone mass was not, however, significantly different from normal in the women with endometriosis who were not treated with clomiphene. The magnitude of the increase in trabecular bone mass was dramatic, i.e., equivalent to as much as a 50% increase in contrast to normal subjects and other women with endometriosis who had not been treated with the drug "CLOMID". Bone density was reported in Hounsfield units (HU). For reference, air has a value of $-1000$ HU and water is set at 0 HU. Mean ($\pm$SD) of these results are shown below:

TABLE 1

Mean Cortical and Trabecular Bone Mass in Women with Endometriosis

| | Cortex (HU) | Trabecular (HU) | |
|---|---|---|---|
| | Number of Subjects | Age (years) | Cortex (HU) | Trabecular (HU) |
| Normal | 10 | 31.7 ± 4 | 1267 ± 69 | 212 ± 51 |
| Endometriosis | | | | |
| No clomiphene | 17 | 29.6 ± 5 | 1105 ± 106* | 173 ± 68 |
| Clomiphene | 3 | 30.3 ± 3 | 1137 ± 44 | 310 ± 64* |

*$p < 0.05$ when compared to normal conditions.

EXAMPLE 2

Treatment of Women with Endometriosis

Cortical bone mass was found to be significantly decreased in women with endometriosis, (F. Comite, P. Jensen, K. Hutchinson, M. L. Polan, F. Haseltine and A. DeCherney, "Reduced Cortical Bone Mass in Endometriosis", (In) *Society for Gynecologic Investigation*", Toronto, March, 1986, #357), comparable to that noted in the perimenopausal subjects. None of the twenty women treated were cigarette smokers. To applicants' knowledge endometriosis has heretofore not been described as a potential risk factor for osteoporosis.

Random hormonal measurements were obtained in the women with endometriosis. Mean serum estradiol ($E_2$) was 100±36 pg/ml and progesterone (P) was 4.1±2.3 ng/ml. Although these values were within the normal range for the date of the last known menstrual cycle, they tended to be at the lower end of the normal range. All women cycled regularly, however, eleven of the twenty subjects were infertile secondary to endometriosis. Fertility had not been determined in the nine remaining subjects, who had presented for treatment of pelvic pain secondary to endometriosis. Decreased cortical bone mass is known to occur in association with estrogen deficiency, (J. A. Schlechte, B. Sherman and R. Martin, "Bone Density in Amenorrheic Women with and without Hyperprolactinemia", *J. Clin. Endocrinol. Metab.*, 56, 1120-1123, (1983)). Although random estradiol levels were normal in this group of women with endometriosis, mean intergrated estradiol levels over time are unknown. However, this decrease in cortical bone suggests uncoupling of the normal bone resorption-formation sequence similar to that seen in perimenopausal women. Trabecular bone is reported to be acutely affected by surgically induced menopause, (A. Horsman, M. Simpson, P. A. Kirby and B. E. C. Nordin, "Non-linear Bone Loss in Oophorectomized Women", *Br. J. Radiol.*, 50, 504, (1977)). However, cortical bone mass appears to decrease while trabecular bone is maintained in the period prior to the onset of menopause. It may be that cortical bone changes reflect the more subtle decrease in estradiol, such as that which occurs as women move from pre- to peri- to the postmenopausal period.

Trabecular bone mass was not significantly different from normal in the women with endometriosis who were not treated with clomiphene. However, there was a dramatic increase in the trabecular bone mass in three women who had been treated with clomiphene in the past and had conceived following this therapy.

EXAMPLE 3

Treatment of Women without Endometriosis

Measurements of QCT of the distal radius in a group of fertile and infertile patients previously treated with clomiphene (within a period of six months to two years) were obtained to determine a possible link between clomiphene and increased bone mass. This was a retrospective study which evolved as a result of the increased trabecular bone noted in the women with endometriosis who had been treated with clomiphene. It was believed that, although clomiphene is a mixed estrogen agonist-antagonist, it might have estrogen-like effects on the bone. Eight of the twenty women had successfully sustained a pregnancy following the clomiphene therapy. Twelve women have remained nulliparous.

TABLE 2

| | Number of Subjects | Age (years) | Cortex (HU) | Trabeculae (HU) |
|---|---|---|---|---|
| Normal | 10 | 31.7 ± 4 | 1267 ± 69 | 212 ± 51 |
| Infertility + Clomiphene | | | | |
| No pregnancy | 12 | 31.5 ± 4 | 1098 ± 132* | 150 ± 54* |
| Pregnancy | 8 | 33.3 ± 3 | 1184 ± 70 | 280 ± 45* |

Mean ± SD *$p < 0.05$ when compared to normal controls

TABLE 3

Summary of Quantitative Computed Tomography (QCT) Data

|  | Number of Subjects | Age (years) | Cortex (HU) | Trabeculae (HU) |
|---|---|---|---|---|
| Normal (CRC Study) | 20 | 31.3 ± 4 | 1244 ± 85 | 206 ± 39 |
| Normal Non-smoking | 10 | 31.7 ± 4 | 1267 ± 69 | 212 ± 51 |
| Irregular Menses | 8 | 30.7 ± 4 | 1186 ± 120 | 157 ± 55* |
| Primary Amenorrhea | 9 | 25.7 ± 6 | 911 ± 111* | 66 ± 45* |
| Perimenopausal | 10 | 48.8 ± 2 | 1089 ± 58* | 198 ± 26 |
| Postmenopausal | 20 | 64.7 ± 8 | 835 ± 160* | 72 ± 69* |
| *Endometriosis* | | | | |
| No clomiphene | 17 | 29.6 ± 5 | 1105 ± 106* | 173 ± 68 |
| Clomiphene | 3 | 30.3 ± 3 | 1137 ± 44* | 310 ± 64* |
| *Infertility + Clomiphene* | | | | |
| No pregnancy | 12 | 31.5 ± 4 | 1098 ± 132* | 150 ± 54* |
| Pregnancy | 8 | 33.3 ± 3 | 1184 ± 70 | 280 ± 45* |

Mean ± SD *p < 0.05 when compared to normal controls

Cortical and trabecular bone mass was significantly decreased in the group of infertile women treated with clomiphene in contrast to the fertile subjects and normal controls. A significant increase in the trabecular bone mass was demonstrated in the women who were proven to be fertile following clomiphene therapy. This study was limited by the fact that no baseline QCT prior to pregnancy was obtained due to the retrospective design. Therefore, it is not possible to rule out pregnancy as a significant factor in the increase in trabecular bone mass. It is of interest that the cortical bone mass in these women who were fertile was normal. This is in contrast to the significantly reduced cortical bone mass observed in the three fertile women with endometriosis who were also treated with clomiphene. The amount of cortical bone in the fertile women with endometriosis was similar to the cortical bone mass seen in the other women with endometriosis. Without wishing to be bound by any particular theory of operability, this suggests that the factor(s) responsible for the cortical bone reduction in the patients with endometriosis may interfere with the gain in cortical bone that might be induced by clomiphene.

It will be appreciated that the instant specification and claims are set forth by way of illustration and not limitation and that various modifications and changes may be made without departing from the spirit and scope of the present invention.

What is claimed is:

1. A method for predicting fertility in a human female comprising administering to a human female an effective amount of clomiphene or its citrate salt, said effective amount of clomiphene being sufficient to increase the bone mass of a human, said clomiphene being administered alone or in admixture with a diluent and determining if said female experiences increased bone mass, whereby an increase in bone mass would be predictive of fertility.

2. A method according to claim 1, wherein said clomiphene is administered daily.

* * * * *